US011224574B1

(12) United States Patent
Kim

(10) Patent No.: US 11,224,574 B1
(45) Date of Patent: Jan. 18, 2022

(54) GEL-INDUCIBLE COMPOSITION FOR PET ADMINISTRATION ASSISTANCE

(71) Applicant: VALVET KCARE, Seoul (KR)

(72) Inventor: Young Min Kim, Seoul (KR)

(73) Assignee: VALVET KCARE, Seoul (KR)

( * ) Notice: Subject to any disclaimer, the term of this patent is extended or adjusted under 35 U.S.C. 154(b) by 0 days.

(21) Appl. No.: 16/986,686

(22) Filed: Aug. 6, 2020

(51) Int. Cl.
*A61K 9/16* (2006.01)
*A61K 47/36* (2006.01)
*A61K 47/24* (2006.01)
*A61K 47/44* (2017.01)
*A61K 47/42* (2017.01)

(52) U.S. Cl.
CPC .......... *A61K 9/1688* (2013.01); *A61K 47/24* (2013.01); *A61K 47/36* (2013.01); *A61K 47/42* (2013.01); *A61K 47/44* (2013.01)

(58) Field of Classification Search
None
See application file for complete search history.

(56) References Cited

U.S. PATENT DOCUMENTS

2012/0321703 A1    12/2012  Kouri
2014/0363537 A1*   12/2014  Doerr ............... A23K 20/189
                                            426/63

FOREIGN PATENT DOCUMENTS

CN      109258932 A   *  1/2019
KR         200329124      10/2003
KR      2020170000112       1/2017

OTHER PUBLICATIONS

CN 109258932A Google English Translation. (Year: 2019).*

* cited by examiner

*Primary Examiner* — Kyung S Chang
(74) *Attorney, Agent, or Firm* — Cantor Colburn LLP

(57) ABSTRACT

Provided is a gel-inducible composition for pet administration assistance. The gel-inducible composition for pet administration assistance has a viscosity sufficient to adhere to the ceiling of the pet's mouth by containing an oil component alone or containing a high concentration of a viscosity-adjusting agent in the oil component. When a powdered prescription drug is mixed with the composition, there is no layer separation between the composition and the powdered drug occurs, and when the mixture is scooped up with a finger and applied to the ceiling of the pet's mouth, the mixture completely adheres to the ceiling of the pet's mouth and the drug is naturally absorbed when the composition component melts. Thus, the composition makes it possible to administer the prescription drug at an appropriate dosage.

7 Claims, 3 Drawing Sheets

GEL-INDUCIBLE COMPOSITION FOR PET ADMINISTRATION ASSISTANCE

BACKGROUND

1. Technical Field

The present invention relates to a gel-inducible composition for pet administration assistance, and more particularly to a gel-inducible composition for pet administration assistance, which has a viscosity sufficient to adhere to the ceiling of the pet's mouth by containing an oil component alone or containing a high concentration of a viscosity-adjusting agent in the oil component, and which is configured such that, when a prescription drug is mixed with the composition and the mixture is scooped up with a finger and applied to the ceiling of the pet's mouth, the mixture completely adheres to the ceiling of the pet's mouth without flowing down and the drug is naturally absorbed when the composition component melts.

2. Related Art

In modern society, pets are companion animals that live with people and are represented by dogs and cats. Pets are kept in close relationship with people and grow up while receiving more attention and care than animals from people.

Therefore, when pets that are companion animals are sick due to abnormalities in health, these pets undergo a medical examination in veterinary hospitals and are administered by drugs. However, these drugs are mostly in the form of powders or pills and are administered through the oral cavity. At this time, pets with an excellent sense of smell frequently refuse to take the drugs due to the smell of the drugs, and thus it is inconvenient to administer the drugs through the oral cavity, and the dosage is not reached. For these reasons, improvements are required.

As part of this effort, an oral liquid drug administration container for pets (Patent Document 1) was designed, which can more easily feed pets with liquid drugs or nutrients. It is a method of forcibly administering a liquefied drug, obtained by powdering a drug and mixing the powder with water, to the pet's oral cavity through a spoon for drug administration or a syringe. However, pets are unable to swallow properly due to the smell and bitter taste of the drug administered through the oral cavity and spit out the administered drug again, making it actually difficult to treat the pets with the drug. In particular, a problem arises in that, if a dog or a cat experiences the bitterness of a drug when administering the drug by a syringe, the animal does not come to the guardian even if the guardian merely holds the syringe for second or later administration.

In another attempt, a drug-receiving space is formed in a pet feed, so that a drug in a solid, capsule or powder form can be received in the feed and the pet can take the drug received in the feed when eating the feed, whereby the pet take the drug without aversion (Patent Document 2). Alternatively, a method of administering a drug as a mixture with jam or honey is used. However, in this case, another problem arises in that the jam or honey is harmful to the body because the sugar content thereof is excessively high.

In addition, a frozen capsule formulation containing a drug in a hollow space was proposed, which can be administered orally to a pet (Patent Document 3).

However, it is still difficult to solve the problem that a pet refuses to take a prescription drug when administering the drug to the pet, and thus it is difficult to administer an appropriate dosage of the drug.

Accordingly, the present inventor has made efforts to solve the problems with the conventional art, and as a result, has provided a gel-inducible composition for pet administration assistance, which has a viscosity sufficient to adhere to the ceiling of the pet's mouth by containing an oil component alone or adjusting the viscosity by adding a high concentration of a viscosity-adjusting agent to the oil component, and has found that, when a prescription drug is added to and mixed with the composition and the mixture is scooped up with a finger and applied to the ceiling of the pet's mouth, the mixture completely adheres to the ceiling of the pet's mouth without flowing down and the drug is naturally absorbed when the composition component melts, thereby completing the present invention.

PRIOR ART DOCUMENTS

Patent Documents (Patent Document 1) Korean Utility Model Publication No. 0329124 (Sep. 26, 2003)
(Patent Document 2) Korean Utility Model Application Laid-Open No. 2017-0000112 (Jan. 9, 2017)
(Patent Document 3) US Patent Application Publication No. 2012-0321703 (2012 Dec. 20).

SUMMARY OF THE INVENTION

An object of the present invention is to provide a gel-inducible composition for pet administration assistance.

Another object of the present invention is to provide a packaged gel inducible product for pet administration assistance in which a powdered prescription drug is contained in the gel-inducible composition for pet administration assistance.

To achieve the above objects, the present invention provides a gel-inducible composition for pet administration assistance containing an oil component or containing a silicone-based or a biogum-based viscosity-adjusting agent in the oil component.

The gel-inducible composition for pet administration assistance according to the present invention may further contain an enzyme with the oil component.

The enzyme contained may preferably be any one or more selected from the group consisting of protease, alpha-amylase, cellulase that is an enzyme degrading the dietary fiber cellulose, lipase, and pectinase that is an enzyme degrading the polysaccharide pectin.

The above-described gel-inducible composition for pet administration assistance may have a viscosity of 9,500 to 100,000 cP as measured using a rotational viscometer at a rotating speed of 10 rpm at a temperature of 25° C.

The oil component of the present invention includes a vegetable oil or an animal oil. The vegetable oil is any one selected from the group consisting of canola oil, soybean oil, corn oil, grapeseed oil, and rice bran oil.

In addition, the silicone-based viscosity-adjusting agent is preferably sodium silicoaluminate, and the biogum-based viscosity-adjusting agent is any one selected from the group consisting of xanthan gum, carrageenan, guar gum, diutan gum, cellulose gum, and gellan gum.

The present invention also provides a packaged gel inducible product for pet administration assistance in which a powdered prescription drug is contained in the gel-inducible composition for pet administration assistance in an amount of 5 to 10 wt % based on the standard daily food intake per body weight of a pet.

The packaged gel inducible product is characterized in that it is poorly soluble in an aqueous phase and is soluble in an oil phase.

DETAILED DESCRIPTION

Hereinafter, the present invention will be described in detail.

The present invention provides a gel-inducible composition for pet administration assistance containing an oil component alone or containing a viscosity-adjusting agent in the oil component.

In a first embodiment, the gel-inducible composition for pet administration assistance contains an oil component alone. The oil component includes a vegetable oil or an animal oil. As the vegetable oil, any one selected from the group consisting of canola oil, soybean oil, corn oil, grapeseed oil and rice bran oil is preferably used.

In addition, as the animal oil, any animal oil may be used as long as it maintains a liquid state at room temperature. Examples of animal oils that may be used in the present invention include, but are not limited to, horse oil, squalene, lanolin, and the like.

In a second embodiment, the gel-inducible composition for pet administration assistance according to the present invention further contains a silicone-based or a biogum-based viscosity-adjusting agent in the oil component which is preferably a vegetable oil.

The vegetable oil that is used in the gel-inducible composition for pet administration assistance according to the present invention may be any one selected from the group consisting of canola oil, soybean oil, corn oil, grapeseed oil, and rice bran oil. The oil component may be selected in consideration of compatibility and miscibility between the components of the composition.

In addition, the gel-inducible composition for pet administration assistance according to the first or second embodiment of the present invention is designed to have a necessary viscosity such that, when a powdered drug is mixed with the composition, the mixture is completely scooped up with a finger without flowing down and without leaving residue in the container.

The preferred viscosity of the composition is 9,500 to 100,000 cP as measured using a rotational viscometer at a rotating speed of 10 rpm at a temperature of 25° C., and the composition having a viscosity within the above range is preferable because it may adhere to the ceiling of the pet's mouth. If the viscosity is lower than 9,500 cP, it is impossible to completely scoop up the composition, due to the excessively high flowability of the composition, making it difficult to administer a prescription drug at an appropriate dosage. If the viscosity is higher than 100,000 cP, the composition will be excessively dry and a prescription drug will not mix therewith, making it difficult to administer the drug.

Figure 1:
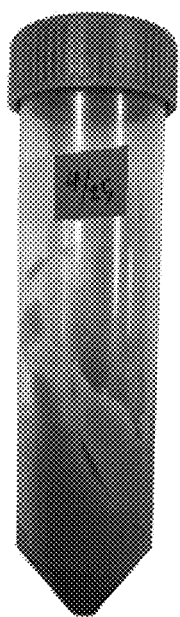
FIG. 1 is a photograph showing a packaged gel inducible product in which a powdered drug is added to a gel-inducible composition for pet administration assistance according to the present invention.

FIG. 1 is a photograph showing a gel formulation in which a powdered drug is added to the gel-inducible composition for pet administration assistance according to the present invention. When the gel formulation is scooped up with a finger and applied to the ceiling of the pet's mouth, the gel formulation (mixture) may adhere to the ceiling of the pet's mouth without flowing down, and the drug may be naturally absorbed when the composition component melts. Thus, the gel formulation makes it possible to administer a prescription drug at an appropriate dosage.

More preferably, the viscosity of the gel-inducible composition for pet administration assistance according to the second embodiment of the present invention is adjusted depending on the content of a silicone-based or biogum-based viscosity-adjusting agent in the oil component. In an example of the present invention, sodium silicoaluminate used as the silicone-based viscosity-adjusting agent is preferably contained in an amount of 20 to 45 parts by weight based on 100 parts by weight of the vegetable oil. In this case, the viscosity within the above-described range is satisfied. If the content of the viscosity-adjusting agent is out of the above-described range, the desired viscosity may not be achieved. That is, it is impossible to achieve a viscosity at which a mixture of the composition and a prescription drug is completely scooped up with a finger without leaving residue in the container.

In addition, when xanthan gum is used as the viscosity-adjusting agent in an example of the present invention, the desired viscosity is satisfied when xanthan gum is contained in an amount of 110 to 160 parts by weight based on 100 parts by weight of the vegetable oil.

An example of the present invention describes the use of canola oil, but is not limited thereto.

The silicone-based viscosity-adjusting agent is preferably sodium silicoaluminate containing $Na_2O:Al_2O_3:SiO_2$ at a molar ratio of 1:1:13.

The sodium silicoaluminate is a white fine amorphous powder or granule, and shows a loss in weight when dried at 105° C. for 2 hours. Here, the loss in weight should be less than 8.0 wt %. When the sodium silicoaluminate is quantitatively analyzed after dried at 105° C. for 2 hours, it contains 6.0 to 76.0 wt % of silicon dioxide ($SiO_2$), 9.0 to 13.0 wt % of aluminum oxide ($Al_2O$), and 4.0 to 7.0 wt % of sodium oxide ($Na_2O$).

In addition, the sodium silicoaluminate is dried at 150° C. for 2 hours and then 5 g is weighed precisely and heated at 90° C. until the above-described contents are reached, the loss in weight thereof should satisfy the requirement of 8.0 to 13.0 wt %.

In addition, the biogum-based viscosity-adjusting agent used in the present invention may be any one selected from the group consisting of xanthan gum, carrageenan, guar gum, diutan gum, cellulose gum, and gellan gum. Xanthan gum is used in an example of the present invention, but is not limited thereto.

The gel-inducible composition for pet administration assistance according to the first or second embodiment of the present invention may further contain a mixed enzyme preparation.

The enzyme is a protein that helps to obtain energy by hydrolyzing a high molecular organic compound of food into a low molecular organic compound in the digestive tract of an animal. The enzyme that may be contained in the composition may be selected from the group consisting of protease, alpha-amylase, cellulase that is an enzyme degrading the dietary fiber cellulose, lipase, and pectinase that is an enzyme degrading the polysaccharide pectin.

In addition, when the composition according to the present invention contains mixed lactic acid bacteria together with the enzyme, it may provide a balance between in vivo degradation, and digestion and toxin release, in particular, and may be administered to, inter alia, dogs or cats with thin stools or diarrhea, cats or dogs in need of prevention of enteritis, old dogs with weak intestines, or dogs or cats with reduced immunity.

In addition, the composition according to the present invention may contain chicken liver powder and conventional additives such as dextrose monohydrate, an emulsifying agent and a preservative.

The chicken liver powder is an excellent source of protein, is rich in vitamin A and vitamin B, especially vitamin B12, contains trace elements such as iron, copper, zinc, chromium, may be stored as spray-dried powder for a long period of time, and is easy to use in all seasons.

The present invention also provides a packaged gel inducible product for pet administration assistance in which a powdered prescription drug is contained in the gel-inducible composition for pet administration assistance according to the first or second embodiment of the present invention in an amount of 5 to 10 wt % based on the standard daily food intake of a pet.

Although the kind of powdered prescription drug is not particularly limited, preferred examples of the powdered prescription drug include powdered drugs for prevention or treatment of eye, joint, skin, liver, kidney, heart or dental diseases.

The drugs that are good for the eyes include lutein and astaxanthin, and the drugs that are good for joints include green mussel and glucosamine. The drugs that are good for the skin include aloe, cysteine, and L-methionine, the drugs that are good for the liver include milk thistle, L-carnitine, and omega-3 fatty acids, and the drugs that are good for kidneys include omega-3 fatty acids, vitamin B groups, and antioxidants. In addition, the drugs that are good for the heart include L-carnitine, taurine, green tea extract (polyphenol), rosemary extract (polyphenol). Mutanase (plaque removing enzyme) and celery oil may be used as drugs for prevention of mouth ulcer and gum inflammation in dogs or cats.

At this time, the formulation of the packaging is not particularly limited, but is preferably a paste gel formulation which may be provided as a disposable stick packaging, toothpaste packaging, or the like.

In addition, according to the present invention, the gel-inducible composition for pet administration assistance and a powdered prescription drug are introduced, and then mixed together to form a gel. The gel may be scooped up with a finger and attached to the ceiling of the pet's mouth, thereby administering the prescription drug at an appropriate dosage.

That is, when a prescription drug is powdered, the present invention may provide a gel-type formulation by predetermining the optimum viscosity of the gel-forming composition for facilitating pet drug administration, at which the composition is neither dry not flow down when mixed with the drug, and mixing the composition with the drug by a simple mixing means.

Figure 2:
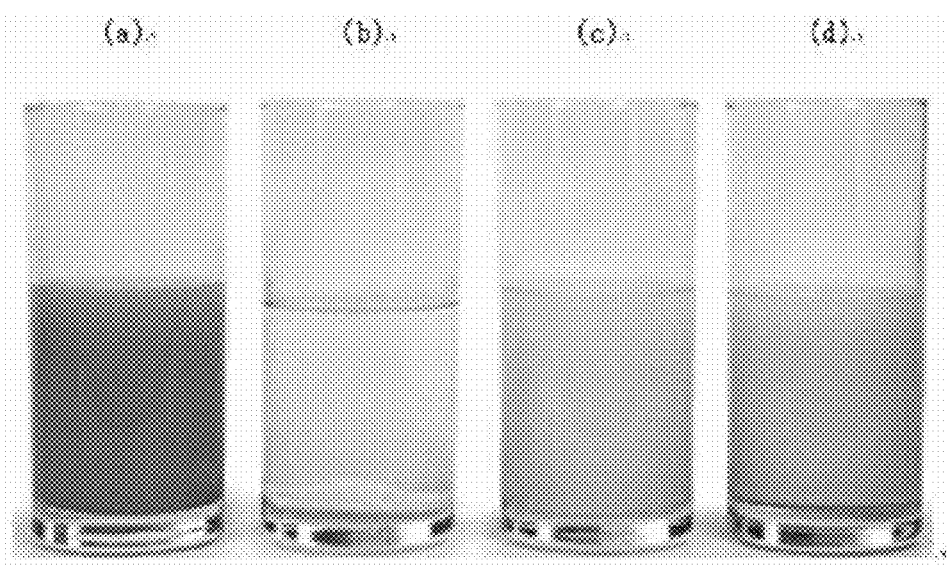
FIG. 2 depicts photographs showing the dissolution behavior of a mixture of a gel-inducible composition for pet administration assistance according to the present invention and a powdered drug in an aqueous phase.

FIG. 2 depicts photographs showing the dissolution behavior of a mixture of the gel-inducible composition for pet administration assistance according to the present invention and a powdered drug in an aqueous phase. As can be seen therein, the mixture does not dissolve at all in the aqueous phase.

Thus, as the composition of the present invention contains the oil component as a main component, a powdered drug mixed with the composition is completely coated with the oil component, so that it does not dissolve even in water. Thus, the composition of the present invention may provide a formulation that allows the powdered drug to be safely delivered to the intestine by blocking contact with gastric acid and absorbed in the intestine. Accordingly, the composition of the present invention may achieve a higher blood concentration of a drug than when the drug is administered by other methods.

Figure 3:
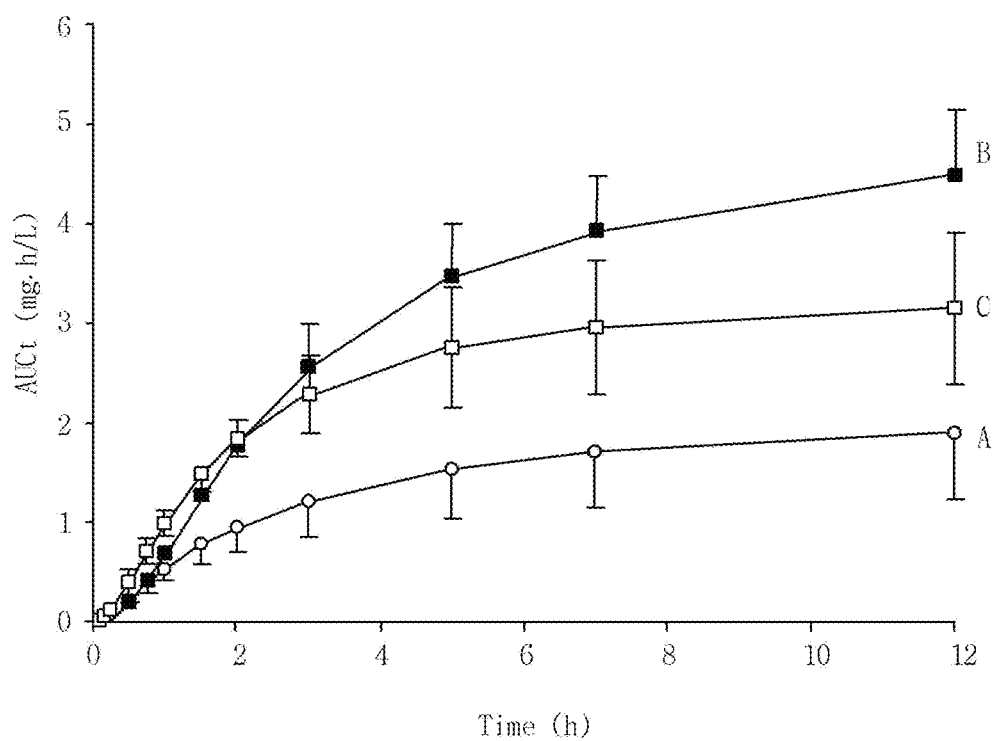
FIG. 3 shows in vivo pharmacokinetics (AUC results) of enrofloxacin with time after administration of a mixture of a gel-inducible composition for pet administration assistance according to the present invention and the powdered prescription drug enrofloxacin (5 mg/kg) to experimental animals.

FIG. 3 shows the results of measuring $AUC_t$ (n=4, mean+/−s.d.) among in vivo pharmacokinetic parameters of enrofloxacin with time after administration of a mixture of the gel-inducible composition for pet administration assistance according to the present invention and the powdered prescription drug enrofloxacin (5 mg/kg) to experimental animals.

Referring to FIG. 3, the antibiotic enrofloxacin powdered drug was mixed with each of compositions prepared in Examples 2 and 11, and then administered to experimental animals (B and C in FIG. 3), and as a result, it could be confirmed that the initial concentration of the drug in the blood was relatively high and the concentration was persistent, compared to those in a control group (A in FIG. 3) in which the drug was mixed with sterile distilled water Hereinafter, the present invention will be described in more detail with reference to examples. However, these examples are only to explain the present invention in more detail, and the scope of the present invention is not limited thereto.

Example 1

Among the components shown in Table 1 below, components excluding sodium silicoaluminate were introduced into a container in the amounts shown in Table 1, and then mixed together at 20° C. for 60 minutes. Next, an aging step was performed, and the components were mixed while sodium silicoaluminate (loss in weight on drying: 6 wt %; average particle diameter: 8 μm; pH 10) was added slowly thereto, thereby preparing the composition of the present invention.

TABLE 1

| Component | Content (wt %) | Content (parts by weight) |
|---|---|---|
| Canola oil | 68.30 | 100 parts by weight |
| Sodium silicoaluminate | 13.64 | 20 parts by weight |

TABLE 1-continued

| Component | Content (wt %) | Content (parts by weight) |
|---|---|---|
| Sugar (dextrose monohydrate) | 5.90 | 8.6 parts by weight |
| Chicken liver powder | 3.00 | 4.4 parts by weight |
| Mixed enzyme preparation | 2.10 | 3.1 parts by weight |
| Preservative | 0.10 | 0.15 parts by weight |
| Emulsifying agent | 0.10 | 0.15 parts by weight |

Examples 2 to 4

Compositions were prepared in the same manner as in Example 1, except that the content of sodium silicoaluminate based on 100 parts by weight of canola oil was changed as shown in Table 3 below.

Comparative Examples 1 and 2

Compositions were prepared in the same manner as in Example 1, except that except that the content of sodium silicoaluminate based on 100 parts by weight of canola oil was changed as shown in Table 3 below.

Examples 5 to 10

Compositions were prepared in the same manner as in Example 1, except that xanthan gum as a viscosity-adjusting agent was used based on 100 parts by weight of the vegetable oil component canola oil of the composition shown in Table 1 above and the content thereof was changed as shown in Table 4.

Comparative Examples 3 to 5

Compositions were prepared in the same manner as in Example 1, except that the content of xanthan gum based on 100 parts by weight of canola oil was changed as shown in Table 4 below.

Example 11

The components shown in Table 2 below were introduced into a container in the amounts shown in Table 2, and then mixed together at 20° C. for 60 minutes. Next, an aging step was performed, thereby preparing a composition.

TABLE 2

| Component | Content (wt%) | Content (parts by weight) |
|---|---|---|
| Canola oil | 84.04 | 100 parts by weight |
| Sugar (dextrose monohydrate) | 5.90 | 14.2 parts by weight |
| Chicken liver powder | 3.00 | 28.0 parts by weight |
| Preservative | 0.10 | 8.40 parts by weight |
| Emulsifying agent | 0.10 | 8.40 parts by weight |

<Experimental Example 1> Viscosity Measurement

For the compositions prepared in the Examples and the Comparative Examples, the viscosity of each composition was measured using a rotational viscometer (BROOKFIELD (USA), Model: RVT).

A spindle was dipped in each composition to be measured so that it was immersed up to the marked portion. The spindle was immersed slightly obliquely so that no bubbles were generated. Since it is general that viscosity greatly changes depending on temperature, the viscosity was measured under the following conditions after temperature stabilization.

After selecting the appropriate spindle and rotating speed (rpm), measurement was started by pressing the motor on/off key, and the value was recorded after waiting until a stable value was reached. The operation was stopped by pressing press the motor on/off key, and the sample was replaced. The conditions are as follows:

1) Spindle No.: No. RV/HA/HB-6
2) Rotating speed (rpm): 10
3) Sample temperature: 25° C.

The results are shown in Tables 3 and 4 below.

TABLE 3

|  | Comparative Example 1 | Compaiative Example 2 | Example 1 | Example 2 | Example 3 | Example 4 |
|---|---|---|---|---|---|---|
| Canola oil content (parts by weight) | 100 | 100 | 100 | 100 | 100 | 100 |
| Sodium silicoaluminate content (parts by weight) | 5 | 10 | 20 | 30 | 40 | 45 |
| Viscosity (cP) | 200 | 1,500 | 10,000 | 38,000 | 80,000 | 100,000 |

TABLE 4

|  | Comparative Example 3 | Comparative Example 4 | Comparative Example 5 | Example 5 | Example 6 | Example 7 | Example 8 | Example 9 | Example 10 |
|---|---|---|---|---|---|---|---|---|---|
| Canola oil content (parts by weight) | 100 | 100 | 100 | 100 | 100 | 100 | 100 | 100 | 100 |

TABLE 4-continued

|  | Comparative Example 3 | Comparative Example 4 | Comparative Example 5 | Example 5 | Example 6 | Example 7 | Example 8 | Example 9 | Example 10 |
|---|---|---|---|---|---|---|---|---|---|
| Xanthan gum content (parts by weight) | 80 | 90 | 100 | 110 | 120 | 130 | 140 | 150 | 160 |
| Viscosity (cP) | 2,500 | 4,500 | 6,100 | 9,700 | 12,900 | 16,500 | 22,500 | 74,000 | 108,000 |

From the results in Tables 3 and 4 above, based on the range that satisfies a viscosity of 9,500 to 100,000 cP (centipoise) as measured using the rotational viscometer at a rotating speed of 10 rpm at a temperature of 25° C., the kind and content of viscosity-adjusting agent in the vegetable oil were determined. Specifically, the compositions of Examples 1 to 4 satisfied the desired viscosity when they contained sodium silicoaluminate in an amount of 20 to 45 parts by weight based on 100 parts by weight of canola oil, and the compositions of Examples 5 to 10 satisfied the desired viscosity when they contained xanthan gum in an amount of 110 to 160 parts by weight based on 100 parts by weight of canola oil.

It was confirmed that the composition having the viscosity within the above-described viscosity range was completely scooped up with a finger without leaving residue in the container and without flowing down.

<Experimental Example 2> Evaluation of Formulation Stability

Generally, when food enters the stomach, the food is crushed finely by gastric motility while it stays in the stomach for 2 hours (liquid food) or 4 hours (solid food). The crushed food is made like soft porridge by secreted mucus, and gastric acid (pH=2 hydrochloric acid) is secreted in the stomach and disinfects the food while the food stays in the stomach for a long time.

For this reason, pharmaceutical drugs, particularly powdered drugs, have been administered to pets in mixtures with wet can feed, honey, jam, water, dry feed, liquid nutrients, snacks, etc. However, it remains a question whether the drug efficacy can be maintained when these formulations and the powdered drugs are mixed and administered.

FIG. 2 depicts photographs showing the dissolution behavior of a mixture of a gel-inducible composition for pet administration assistance according to the present invention and a powdered drug in an aqueous phase.

FIG. 2(a) shows a commercially available liquid product for pet nutrition containing vitamins and essential amino acids as active ingredients; FIG. 2(b) shows the composition of Example 2; FIG. 2(c) shows a commercially available product for a pet snack containing a tuna or chicken extract; and FIG. 2(d) shows a commercially available product for a pet snack containing chicken breast and porcine liver. Specifically, FIGS. 2(a) to 2(d) show the results obtained by mixing the same powdered drug with each of the products in water at 38° C. for 5 minutes and allowing each mixture to stand for 5 minutes.

As a result, it was confirmed that the commercially available products partially dissolved in water or were suspended as emulsions. From this result, it is expected that the powdered drug component may be exposed to gastric acid under mucus (moisture) conditions and may be destroyed to a considerable extent.

On the other hand, it was confirmed that the composition of Example 2 did not dissolve at all in water.

From this result, it is expected that, as the composition of the present invention contains the oil component as a main component, a powdered drug mixed with the composition will be completely coated with the oil component, so that it will not dissolve even in water, and the drug will be poorly soluble in the mucus (moisture) environment in the stomach, will be safely delivered to the intestine by blocking contact with gastric acid and absorbed in the intestine.

Accordingly, the composition of the present invention is a formulation that may achieve a higher blood concentration of a drug than when the same amount of the drug is administered by other methods.

<Experimental Example 3> Pharmacokinetic Analysis

For oral administration of enrofloxacin to a companion animal, such as a dog or a cat, it is inevitable to prescribe enrofloxacin by crushing it into powder and dispensing the powder, due to the low body weight of the animal. However, a phenomenon frequently occurs in which the companion animal refuses to take the drug during administration and the drug is lost during this administration process. In addition, even if the drug is administered, the results of an experiment on how it affects the blood concentration and effect of the drug are significant.

As experimental animals, 9 male beagle dogs found to be clinically healthy in physical examination were used in this clinical experiment. Animals with a history of receiving antibiotics in the last month were not included in the experiment, and the experimental animals were randomly divided into three groups, each consisting of 3 animals. For experimental groups, a powdered antibiotic (enrofloxacin, 5 mg/kg) was mixed with each of the composition of Example 2 and the composition of Example 11, and for a control group, the antibiotic was mixed with sterile distilled water in place of the composition. Each of the mixtures was administered once orally to the experimental animals. 2.4 ml of each mixture was administered to each animal regardless of the body weight.

At each of 0, 15, 30, 45, 60, 90, 120, 180, 300, 420 and 960 minutes after oral administration of the antibiotic and the test products, a blood samples was collected from the jugular veins, placed in a test tube (heparin tube) and centrifuged at 1500 rpm for 5 minutes. The separated plasma was transferred into an E-tube and stored frozen at −80° C. until analysis.

For measurement of the blood concentration of the antibiotic, the time-dependent concentration of enrofloxacin in the plasma was measured using HPLC-MS/MS (API 4000

LC-MS/MS system) [Report on the Results of Research conducted by Kyungpook National University College of Veterinary Medicine, April 2019].

Pharmacokinetic parameters were calculated using a model-independent analysis method. The maximum plasma concentration ($C_{max}$) and the time ($T_{max}$) to reach the maximum plasma concentration were obtained directly from the time-versus-plasma concentration curve of each subject. The elimination rate constant (k) was obtained by least squares of the log-transformed plasma concentration of the elimination phase, and the half-life ($t_{1/2}$) was calculated from 0.693/k.

The area under the concentration-time curve (AUCt) was obtained by the trapezoidal law, and the area under the concentration-time curve extrapolated to infinite time ($AUC_{inf}$) was obtained by adding the value obtained by dividing the final measured concentration by k. The total clearance (Cl) was calculated by dividing $AUC_{inf}$ by dosage. Pharmacokinetic parameters were expressed as the mean and standard deviation of the data obtained from each subject.

The results are shown in Table 6 below and FIG. 3.

TABLE 5

| Experimental group | Composition |
|---|---|
| A | Enrofloxacin (Baytril) powder + sterile distilled water |
| B | Enrofloxacin (Baytril) powder + Example 2 |
| C | Enrofloxacin (Baytril) powder + Example 11 |

TABLE 6

| Parameter | Experimental group A | Experimental group B | Experimental group C |
|---|---|---|---|
| $C_{max}$ (mg/L) | 0.62 ± 0.15 | 1.24 ± 0.10 | 1.32 ± 0.04 |
| $T_{max}$ (h) | 0.75 ± 0.54 | 1.06 ± 0.31 | 0.67 ± 0.29 |
| k (h$^{-1}$) | 0.29 ± 0.02 | 0.30 ± 0.03 | 0.36 ± 0.02 |
| $t_{1/2}$ (h) | 2.41 ± 0.19 | 2.31 ± 0.27 | 1.93 ± 0.12 |
| $AUC_{12\,h}$ (mg · h/L) 1 | 1.90 ± 0.67 | 4.48 ± 0.65 | 3.15 ± 0.76 |
| $AUC_{inf}$ (mg · h/L) | 1.97 ± 0.71 | 4.66 ± 0.74 | 3.20 ± 0.77 |
| Cl (L/h/kg) | 2.81 ± 1.02 | 1.10 ± 0.20 | 1.62 ± 0.34 |

FIG. 3 shows the AUC results among in vivo pharmacokinetic parameters of enrofloxacin with time after administration of a mixture of the gel-inducible composition for pet administration assistance according to the present invention and the powdered prescription drug enrofloxacin (5 mg/kg) to experimental animals.

As a result, when the enrofloxacin powder drug was mixed with the composition of Example 2 and administered to the dogs, the degree of absorption of the drug significantly increased (p<0.005) compared to when the drug was administered as a mixture with the control (drinking water).

In addition, the enrofloxacin powder drug was mixed with the composition of Example 11 and administered to the dogs, the plasma concentration of enrofloxacin tended to increase, but statistical significance was not shown due to large variation between the subjects.

From the above results, it could be confirmed that, when the drug was administered as a mixture with the gel-inducible composition for pet administration assistance according to the present invention, the plasma concentration and degree of absorption of the drug increased compared to when the drug was administered as a mixture with drinking water.

Thus, the composition of Example 2 or 11 may serve as an administration aid, which does not reduce the efficacy of a powdered drug, for a guardian who has difficulty administering a powdered drug.

In particular, it could be confirmed that Example 2 further containing the mixed enzyme preparation in the composition of Example 11 and Example 2 containing canola oil enhanced the absorption ability of the drug component.

<Experimental Example 4> Change in Drug Concentration Between Formulations

A gel inducible product packaged in a stick pack was prepared by mixing the antibiotic enrofloxacin powder drug with the composition prepared in Example 2. The gel inducible product contained 5 mg of enrofloxacin per kg body weight of a dog.

As another test group, a pill formulation of enrofloxacin was mixed with the composition prepared in Example 2, and as a control group, the enrofloxacin powder drug was contained in sterile distilled water. Each of the formulations was administered orally to dogs.

During 12 hours (0, 5, 10, 15, 30, 45, 60, 90, 120, 180, 300, 420 and 720 minutes) after drug administration, blood samples were collected, and the plasma concentration of enrofloxacin in each blood sample was analyzed using HPLC-MS/MS (API 4000 LC-MS/MS system).

The results of the analysis are shown in Table 7 below and FIG. 4.

TABLE 7

Time-dependent changes in concentration (µ/ml) of enrofloxacin in dog plasma

| Time (min) after drug administration | Control group Water + powdered drug | Test group A Example 2 + powdered drug | Test group B Example 2 + pill |
|---|---|---|---|
| 0 | 0 | 0 | 0 |
| 5 | 49 | 57 | 0 |
| 10 | 721 | 63 | 712 |
| 15 | 772 | 157 | 996 |
| 30 | 706 | 711 | 1154 |
| 45 | 723 | 943 | 1155 |
| 60 | 708 | 1137 | 1046 |
| 90 | 502 | 1214 | 979 |
| 120 | 398 | 1011 | 702 |
| 180 | 288 | 708 | 452 |
| 300 | 155 | 316 | 242 |
| 420 | 86 | 195 | 102 |
| 720 | 29 | 47 | 31 |

Figure 4:
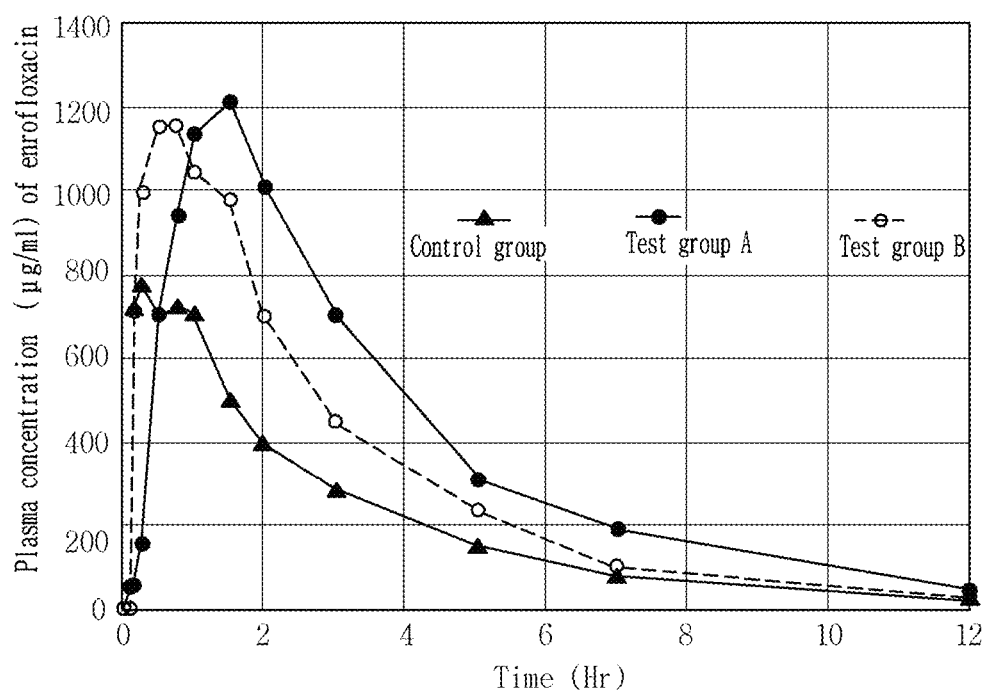
FIG. 4 shows the plasma concentration of a powdered prescription drug with time after administration of different formulations, each comprising a mixture of a gel-inducible composition for pet administration assistance according to the present invention and the drug.

FIG. 4 shows the plasma concentration of the powdered prescription drug with time after administration of different formulations, each comprising a mixture of the gel-inducible composition for pet administration assistance according to the present invention and the drug. From the above results, it can be seen that test group A obtained by mixing the powdered drug with the composition prepared in Example 2 exhibited a significantly high initial plasma concentration of the drug component.

As described above, the gel-inducible composition for pet administration assistance according to the present invention may exhibit a viscosity sufficient to adhere to the ceiling of the pet's mouth by containing an oil component alone or containing a high concentration of a viscosity-adjusting agent in the oil component.

In addition, the gel-inducible composition for pet administration assistance according to the present invention may further contain a powdered prescription drug, and when the composition is scooped up with a finger and applied to the ceiling of the pet's mouth, the mixture of the composition and the prescription drug may completely adhere to the ceiling of the pet's mouth without flowing down, and the drug may be naturally absorbed when the composition melts. Thus, the composition makes it possible to administer the prescription drug at an appropriate dosage.

Therefore, the gel-inducible composition for pet administration assistance according to the present invention may increase digestion and absorption by adding a taste that a pet likes or by adding an enzyme, and may be provided as a pet-specific formulation having a desired viscosity by simple mixing with a dosage of a powdered drug prepared in a veterinary hospital.

Although the present invention has been described in detail only with respect to the described embodiments, it is apparent to those skilled in the art that various changes and modifications are possible without departing from the technical spirit and scope of the present invention, and these changes and modifications fall within the scope of the appended claims.

What is claimed is:

1. A gel-inducible composition being capable of pet administration with a powdered prescription drug, the gel-inducible composition comprising:
   an oil component including a vegetable oil, the vegetable oil being at least one selected from the group consisting of canola oil, soybean oil, corn oil, grapeseed oil, and rice bran oil;
   a silicone-based viscosity-adjusting agent or a biogum-based viscosity-adjusting agent, wherein the silicone-base viscosity-adjusting agent is sodium silicoaluminate contained in 20 to 45 parts by weight based on 100 parts by weight of the oil component, and the biogum-based viscosity-adjusting agent is xanthan gum contained in 110 to 160 parts by weight based on 100 parts by weight of the oil component; and
   a viscosity of 9,500 to 100,000 cP as measured using a rotational viscometer at a rotating speed of 10 rpm at a temperature of 25° C.,
   wherein the powdered prescription drug includes enrofloxacin lutein, astaxanthin, green mussel, glucosamine, aloe, cysteine, L-methionine, milk thistle, L-carnitine, omega-3 fatty acids, vitamin B groups, antioxidants, taurine, green tea extract, rosemary extract, mutanase, and celery oil.

2. The gel-inducible composition claim 1, further comprising: an enzyme.

3. The gel-inducible composition of claim 2, wherein the enzyme is at least one selected from the group consisting of protease, alpha-amylase, cellulase that is an enzyme degrading dietary fiber cellulose, lipase, and pectinase degrading polysaccharide pectin.

4. A packaged gel inducible product being capable of pet administration, the packed gel inducible product comprising:
   the gel inducible composition of claim 1; and
   the powdered prescription drug in an amount of 5 to 10 wt % based on a standard daily food intake per body weight of a pet.

5. The packaged gel inducible product claim 4, wherein the gel inducible product is poorly soluble in an aqueous phase and is soluble in an oil phase.

6. The gel-inducible composition of claim 4, further comprising: an enzyme.

7. The gel-inducible composition of claim 6, wherein the enzyme is at least one selected from the group consisting of protease, alpha-amylase, cellulase degrading dietary fiber cellulose, lipase, and pectinase degrading polysaccharide pectin.

* * * * *